US005476874A

United States Patent [19]

Hungate et al.

[11] Patent Number: 5,476,874

[45] Date of Patent: Dec. 19, 1995

[54] NEW HIV PROTEASE INHIBITORS

[75] Inventors: Randall W. Hungate, Lansdale; Joseph P. Vacca, Telford, both of Pa.

[73] Assignee: Merck & Co., Inc., Rahway, N.J.

[21] Appl. No.: 263,621

[22] Filed: Jun. 22, 1994

[51] Int. Cl.$^6$ .......................... A61K 31/16; C07C 229/00

[52] U.S. Cl. .......................... 514/599; 514/617; 514/630; 560/43; 564/91; 564/92; 562/444

[58] Field of Search ................................ 560/43; 564/91, 564/92; 562/444; 514/599, 617, 630

*Primary Examiner*—C. Warren Ivy

*Assistant Examiner*—Amelia Owens

*Attorney, Agent, or Firm*—Roy D. Meredith; Jack L. Tribble

[57] ABSTRACT

Oligopeptide analogs containing sulfonamide, urea or carbamate linkages in the backbone are described. These compounds are useful in the inhibition of HIV protease, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

4 Claims, No Drawings

NEW HIV PROTEASE INHIBITORS

This application is related to Merck case 18882, U.S. Ser. No. 017,090, filed 02/12/93; 18882IA, U.S. Ser. No. 191,676, filed 02/03/94; 18996, U.S. Ser. No. 059,038, filed 05/07/93; 18996IA, U.S. Ser. No. 235,576, filed 04/29/94.

The present invention is concerned with compounds which inhibit the protease encoded by human immunodeficiency virus (HIV). The compounds, or pharmaceutically acceptable salts thereof, are of value in the prevention of infection by HIV, the treatment of infection by HIV and the treatment of the resulting acquired immune deficiency syndrome (AIDS).

The present invention also relates to pharmaceutical compositions containing the compounds, and to a method of use of the present compounds and other agents for the treatment of AIDS & viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N.E., et. al., Proc. Natl. Acad. Sci. USA, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277( 1985)]. Amino acid sequence homology provides evidence that the pol sequence encodes reverse transcriptase, an endonuclease and an HIV protease [Toh, H. et al., EMBO J. 4, 1267 (1985); Power, M.D. et al., Science, 231, 1567 (1986); Pearl, L. H. et al., Nature 329, 351 (1987)]. Applicants demonstrate that the compounds of this invention are inhibitors of HIV protease.

The compounds of the present invention contain sulfonamide, urea or carbamate linkages in the peptide analog backbone.

BRIEF DESCRIPTION OF THE INVENTION

Compounds of Formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, hydrates or esters, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with the compounds of Formula I, combinations thereof, or pharmaceutically acceptable salts thereof, in the inhibition of HIV protease, the prevention of infection by HIV, the treatment of infection by HIV and in the treatment of the resulting acquired immune deficiency syndrome (AIDS). Compounds of formula I are defined as follows:

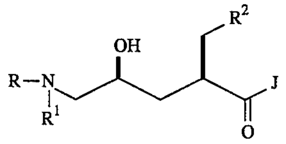

Formula I

Wherein

R is
- a) —V—$R^3$; wherein V is —C(O)—Q—, or —$SO_2$—Q—;

Q is
- a) absent, —O—, or —NH—, $R^1$ is
- a) hydrogen, or
- b) —$C_{1-5}$alkyl unsubstituted or substituted with one or more of
  - i) halo,
  - ii) hydroxy,
  - iii) $C_{1-3}$ alkoxy,
  - iv) aryl unsubstituted or substituted with one or more of $C_{1-4}$alkyl, $C_{1-4}$alkoxy, nitro, amino, amido, carboxy, hydroxy, halo or aryl;
  - v) —W-aryl or W-benzyl, wherein W is —O—, —S—, or —NH—; or
  - vi) heterocycle, unsubstituted or substituted with one or more of $C_{1-4}$alkyl, hydroxy or halo;
  - viii) carboxyl;
- c) —$C_{3-5}$cycloalkyl, unsubstituted or substituted at the 3-position with $C_{1-4}$alkyl; or
- d) aryl unsubstituted or substituted with one or more of $C_{1-4}$alkyl, $C_{1-4}$alkoxy, nitro, amino, amido, carboxy, hydroxy, halo or aryl; and $R^2$ is
- a) phenyl unsubstituted or substituted with one or more of —OH or $C_{1-3}$alkoxy; or
- b) $C_{5-7}$cycloalkyl, unsubstituted or substituted with one or more of —OH or $C_{1-3}$alkoxy;

$R^3$ is
- a) a 5- to 7-membered heterocycle, which heterocycle is unsubstituted or substituted with one or more of —$C_{1-4}$alkyl, oxo, amino or halo;
- b) aryl unsubstituted or substituted with one or more of —$C_{1-4}$alkyl, oxo, amino or halo;
- c) $C_{1-4}$alkyl, unsubstituted or substituted once with aryl or 5- to 7-membered heterocycle;
- d) $C_{3-5}$cycloalkyl, unsubstituted or substituted at the 3-position with $C_{1-4}$alkyl;

J is

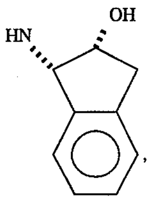,

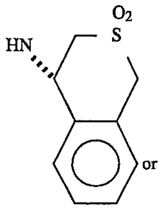 or

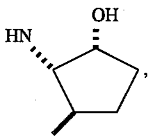, or a pharmaceutically acceptable salt thereof.

The compounds of the present invention may have asymmetric centers and occur as racemates, racemic mixtures and as individual diastereomers or enantiomers, with all isomeric forms being included in the present invention.

When any variable (e.g., heterocycle, $R^1$ or $R^2$, etc.) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. $C_{3-5}$cycloalkyl is a saturated cyclic hydrocarbon ting with the indicated number of carbons. "Halo", as used herein, means fluoro, chloro, bromo or iodo.

As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system any ting of which may be saturated or unsaturated, and which consists of carbon atoms and from one to three heteroatoms selected from the group consisting of N, O and S, and wherein the nitrogen and sulfur heteroatoms may optionally be oxidized, and including any bicyclic group in which any of the above-defined heterocyclic tings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiopyranyl, tetrahydrofuryl, tetrahydropyranyl, and tetrahydrothienyl, thienyl, benzothienyl, thiamorpholinyl, thiamorpholinyl sulfoxide, thiamorpholinyl sulfone and isobenzothiopyranyl.

The pharmaceutically-acceptable salts of the compounds of Formula I (in the form of water- or oil-soluble or dispersible products) include the conventional non-toxic salts or the quaternary ammonium salts of these compounds, which are formed, e.g., from inorganic or organic acids. Examples of such acid addition salts include acetate, adipate, alginate, aspartate, benzoate, bisulfate, citrate, digluconate, dodecylsulfate, fumarate, glycerophosphate, hemisulfate, hydrochloride, 2-hydroxy-ethanesulfonate, lactate, maleate, methanesulfonate, succinate and tartrate.

One preferred embodiment of this invention is compounds of Formula I, wherein

R is a) —V—$R^3$;

wherein

V is —C(O)—Q—, or —$SO_2$—Q—;

Q is a) absent, or —O—, $R^1$ is —$C_{1-5}$alkyl unsubstituted or substituted with one or more of i) aryl unsubstituted or substituted with one or more of $C_{1-4}$alkyl, $C_{1-4}$alkoxy, nitro, amino, amido, carboxy, hydroxy, halo or aryl; or ii) heterocycle, unsubstituted or substituted with one or more of $C_{1-4}$alkyl, hydroxy or halo;

$R^2$ is phenyl unsubstituted or substituted with one or more of —OH or $C_{1-3}$alkoxy; or $R^3$ is a) aryl unsubstituted or substituted with one or more of —$C_{1-4}$alkyl, oxo, amino or halo;

b) $C_{1-4}$alkyl, unsubstituted or substituted once with aryl or 5- to 7-membered heterocycle;

J is

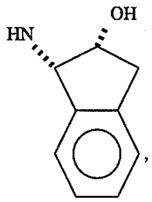, or a pharmaceutically acceptable salt thereof.

Most preferred compounds of this invention include the following:

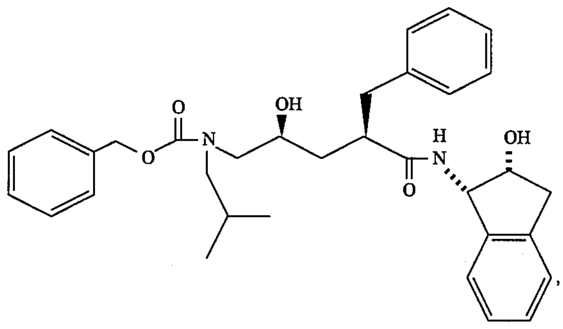, named N-(2'(R)-hydroxy-1'(S)-indanyl)-2(R)-phenylmethyl-4(S)-hydroxy-5-[((2'''-methyl) propyl)-benzyloxycarbonyl]-amino-pentaneamide, or pharmaceutically acceptable salt thereof;

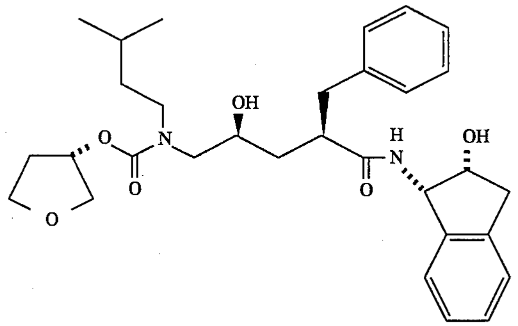
named N-(2'(R)-hydroxy-1'(S)-indanyl)-2(R)-phenylmethyl-4(S)-hydroxy-5-[((2'''-methyl) butyl)-3'(S)-(tetrahydrofuranyloxy)carbonyl]amino-pentaneamide, yl]amino-pentaneamide,
or pharmaceutically acceptable salt thereof.
The compounds of the present invention include but are not limited to those of the following Tables 1–4:
TABLE
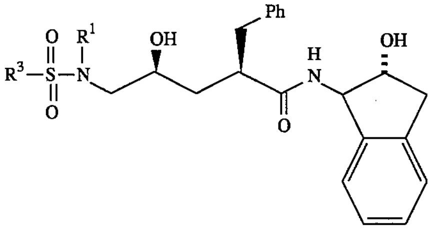
| $R^1$ | $R^3$ |
|---|---|
| 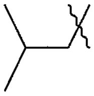 | 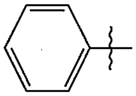 |
| 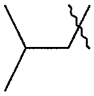 | 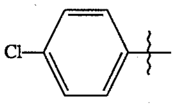 |
| 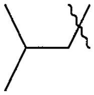 | 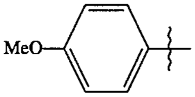 |
| 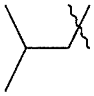 | 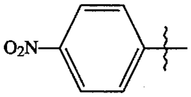 |
| 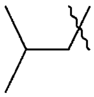 | 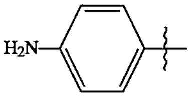 |
| 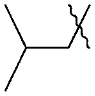 | 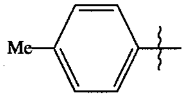 |
| 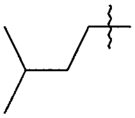 | 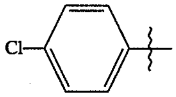 |
TABLE-continued
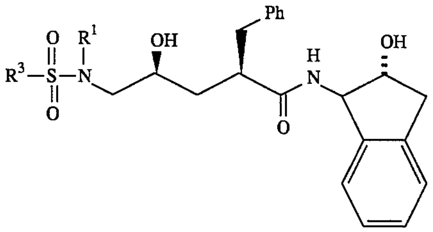
| $R^1$ | $R^3$ |
|---|---|
| 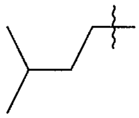 | 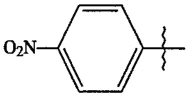 |
| 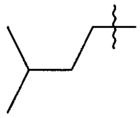 | 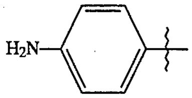 |
| 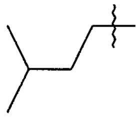 | 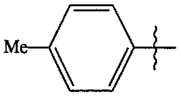 |
| 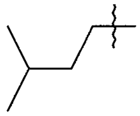 | 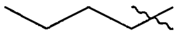 |
| 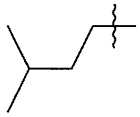 | 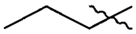 |
| 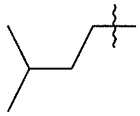 | 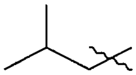 |
| 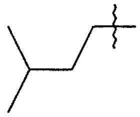 | 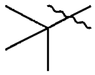 |
| 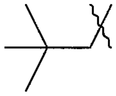 | 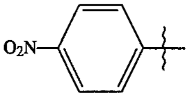 |
| 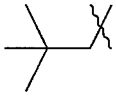 | 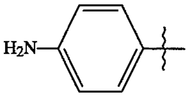 |
| 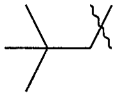 | 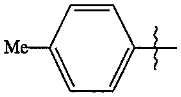 |

TABLE-continued
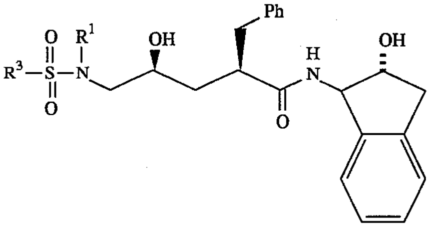
| $R^1$ | $R^3$ |
|---|---|
| 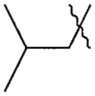 | $CH_3$ |
| 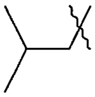 | $CH_3CH_2$ |
| 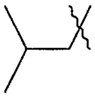 | $CH_3CH_2CH_2$ |
| 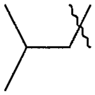 | $CH_3CH_2CH_2CH_2$ |
| 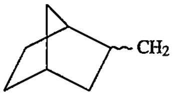 | $CH_3$ |
| 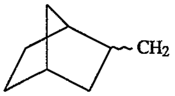 | 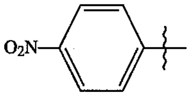 |
| 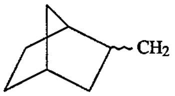 | 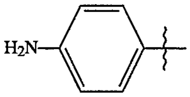 |
| 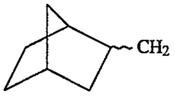 | 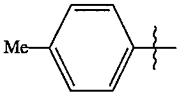 |
| 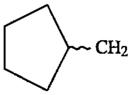 | 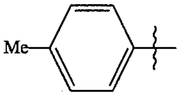 |
| 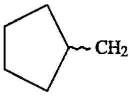 | 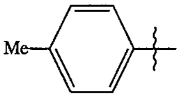 |
| 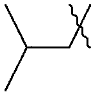 | 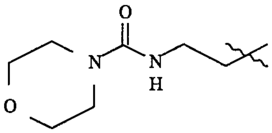 |
| 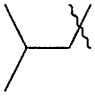 | 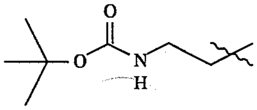 |
TABLE-continued
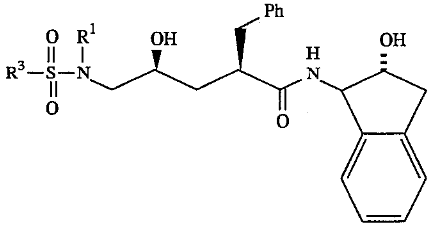
| $R^1$ | $R^3$ |
|---|---|
| 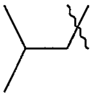 | 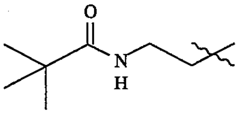 |
| 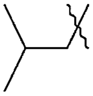 | 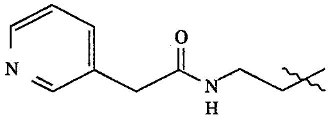 |
| 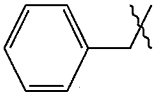 | 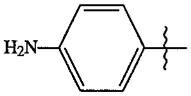 |
| 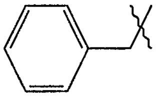 | $CH_3$ |
TABLE 2
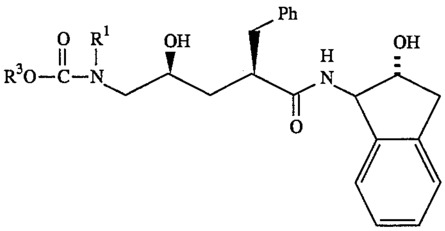
| $R^1$ | $R^3$ |
|---|---|
| 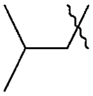 | 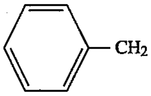 |
| 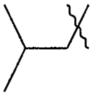 | 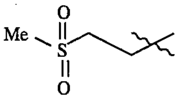 |
| 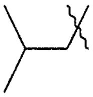 | 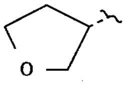 |
| 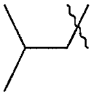 | 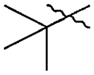 |

TABLE 2-continued
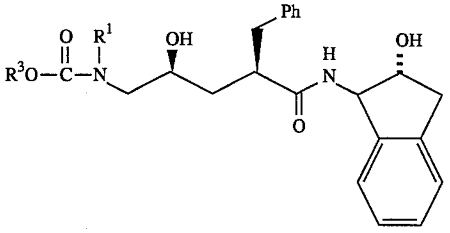
| $R^1$ | $R^3$ |
|---|---|
| 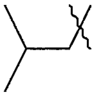 | 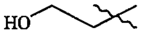 |
| 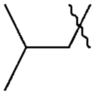 | 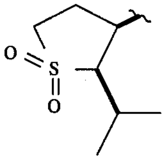 |
| 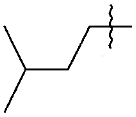 | 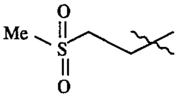 |
| 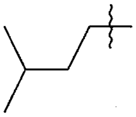 | 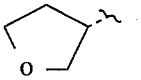 |
| 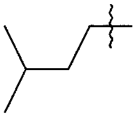 | 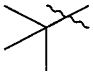 |
| 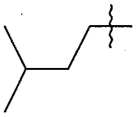 | 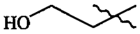 |
| 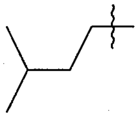 | 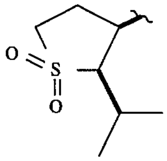 |
| 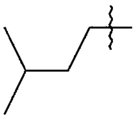 | 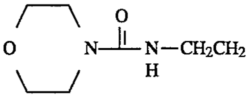 |
| 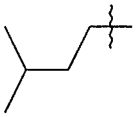 | 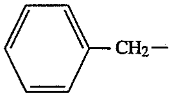 |
TABLE 3
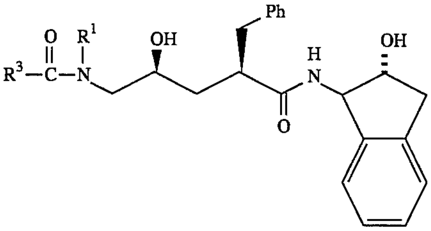
| $R^1$ | $R^3$ |
|---|---|
| 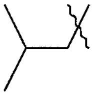 | $CH_3$ |
| 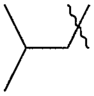 | $CH_3CH_2CH_2CH_2$ |
| 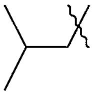 | 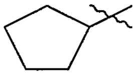 |
| 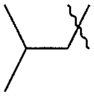 | 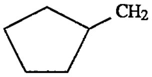 |
| 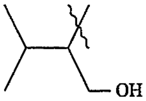 | 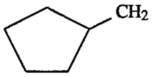 |
| 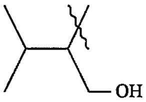 | 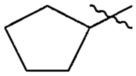 |
| 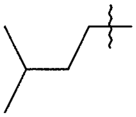 | 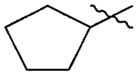 |
| 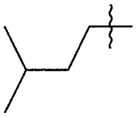 | 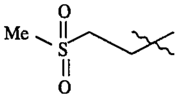 |
| 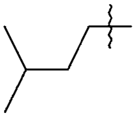 | 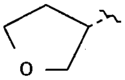 |
| 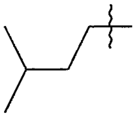 | 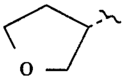 |
| 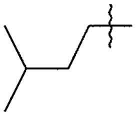 | 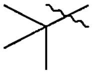 |

TABLE 3-continued

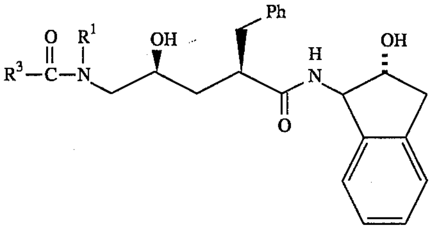

| $R^1$ | $R^3$ |
|---|---|
| 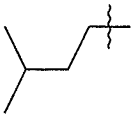 | 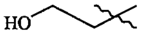 |
| 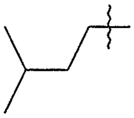 | 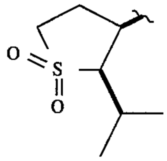 |
| 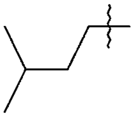 | 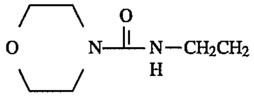 |
| 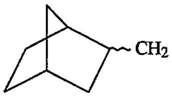 | 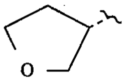 |
| 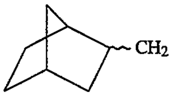 | 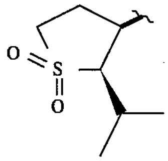 |

TABLE 4

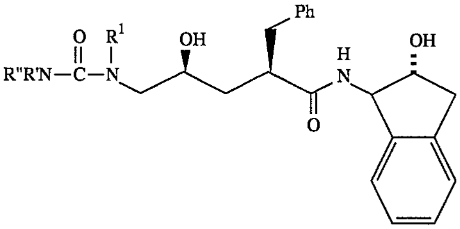

| $R^1$ | R' | R" |
|---|---|---|
| isobutyl | H | tertbutyl |
| isobutyl | H | benzyl |
| isobutyl | H | n-butyl |
| isobutyl | H | cyclopentyl |
| isobutyl | H | phenyl |
| isobutyl | H | 3-pyridylmethyl |
| 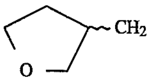 | H | benzyl |

TABLE 4-continued

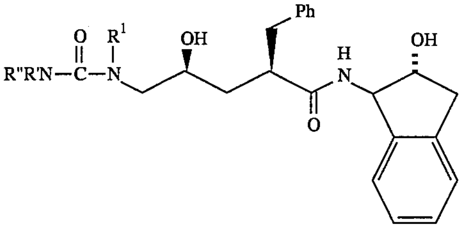

| $R^1$ | R' | R" |
|---|---|---|
| 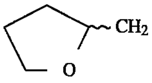 | H | benzyl |
| 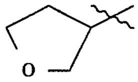 | H | benzyl |
| 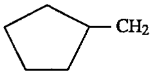 | H | benzyl |
| 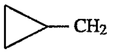 | H | 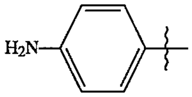 |
| 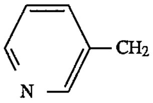 | H | benzyl |
| 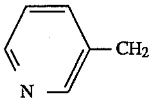 | H | tertbutyl |
| 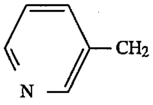 | H | 3-pyridylmethyl |
| 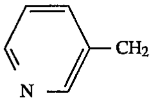 | H | 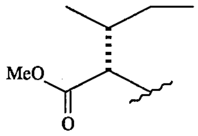 |
| isobutyl | 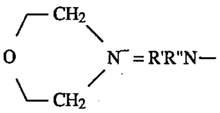 | |

The compounds of the present invention are prepared in accordance with Schemes I–II.

SCHEME 1

Synthesis of

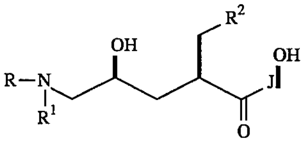

-continued
SCHEME 1

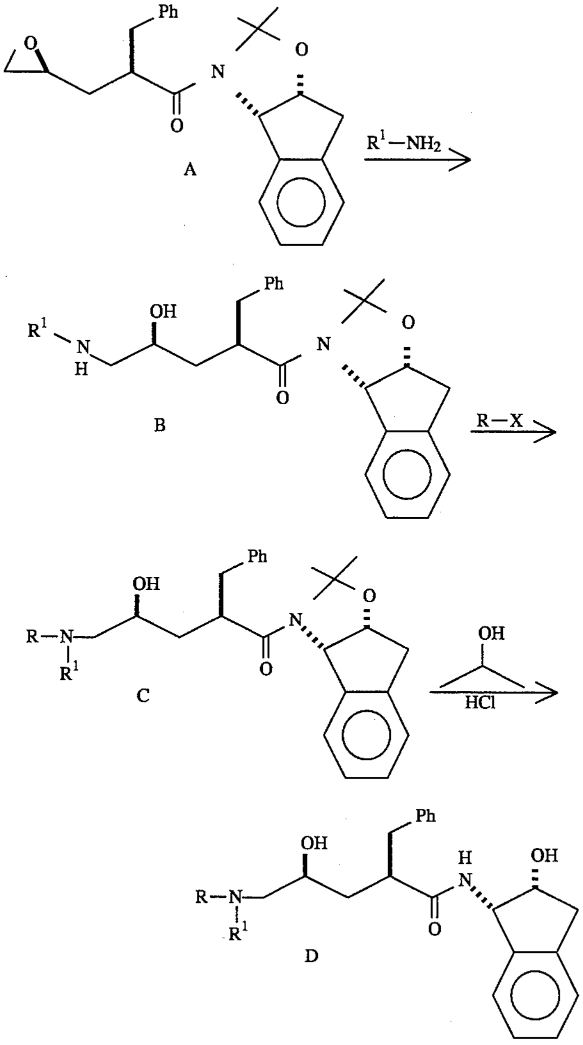

Compounds of Formula 1 are synthesized by the general method outlined in Scheme I. Briefly, the epoxide compound A is synthesized according to EP 054 1168, herein incorporated by references for these purposes. It is reacted at refluxing temperature with an excess of a primary amine, e.g., isobutyl amine, in an alcoholic solvent such as isopropanol. The isolated amine B is then reacted with the appropriate acylating agent. For the synthesis of Formula I compounds with urea linkages, t-butyl isocyanate is the appropriate acylating agent. For sulfonamide linkages, toluene-sulfonyl chloride. For amides, the appropriate acylating agent is a peptide coupling reagent such as cyclopentane acetic acid. The isolated compound C is then treated with acid in isopropanol to cleave the acetonide group to afford the desired product. The acetal cleavage step can also be performed after the amine epoxide opening and the resulting amine then directly reacted with the desired acylating agent to give the product as seen in Scheme 2.

SCHEME 2

Alternate Synthesis of

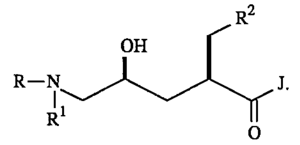

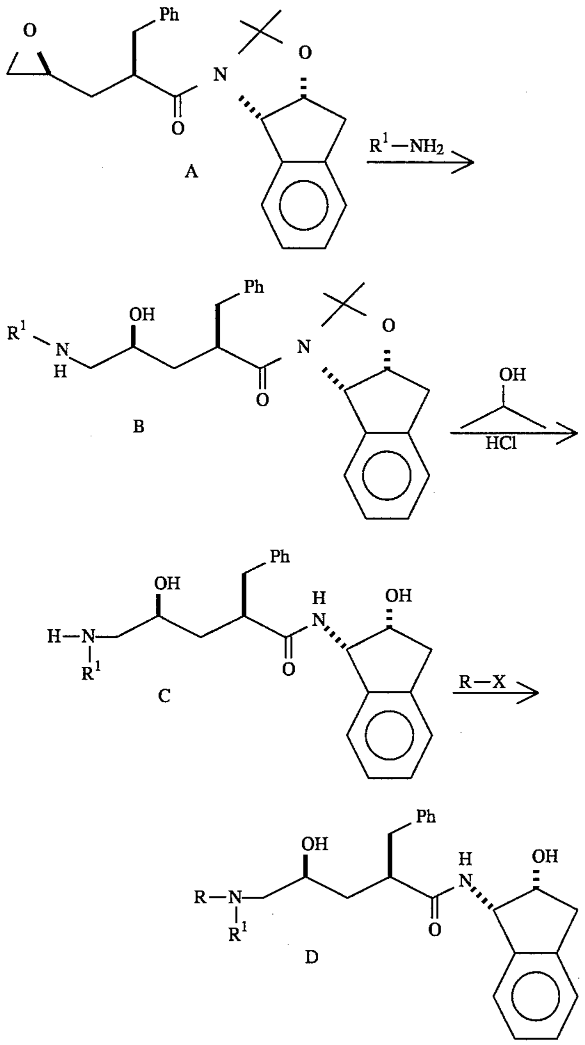

The compounds of the present invention are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, accidental needle stick, or exposure to patient blood during surgery.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

For these purposes, the compounds of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically-acceptable carders, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carder and a therapeutically-effective amount of a compound of the present invention, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| | ANTIVIRALS | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| g4O Cytovene Ganciclovir | Syntex (Palo Alto, CA) | sight threatening CMV peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT AIDS, adv, ARC | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |

TABLE C-continued

| Drug Name | Manufacturer | Indication |
|---|---|---|
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| L-697,661 | Merck (Rahway, NJ) | AIDS, ARC, asymptomatic HIV positive, also in combination with AZT. |
| L-735,524 | Merck (Rahway, NJ) | AIDS, ARC, asymptomatic HIV positive, also in combination with AZT. |
| RO-31-8959 | Hoffmann-LaRoche | AIDS, ARC, asymptomatic HIV positive, also in combination with AZT. |
| | IMMUNO-MODULATORS | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS |
| | | AIDS, in combination w/AZT |
| HIV Core Particle Immunostimulant | Rorer (Ft. Washington, PA) | seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg | AIDS, Kaposi's |

TABLE C-continued

| Drug Name | Manufacturer | Indication |
|---|---|---|
| | (New Orleans, LA) | sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| | ANTI-INFECTIVES | |
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| | OTHER | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table C are the following: L-697,661 or '661' is 3-([4,7-dichloro-1,3-benzoxazol-2-yl)methyl]-amino)-5-ethyl-6-methyl-pyridin -2(1H)-one. The synthesis of L-697,661 is described in EPO 48407 1, and EPO 462800, both herein incorporated by reference. The synthesis of ddC, ddI and AZT are also described in EPO 484071. L-735,524 is

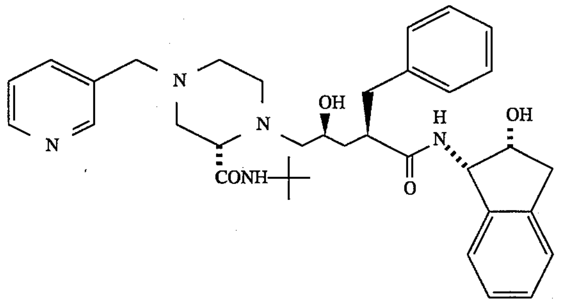

N-(2(R )-hydroxy-1(S)-indanyl)-2(R)-phenylmethyl-4(S)-hydroxy-5-(1-(4-(3-pyridylmethyl)-2 (S)-N'-(t-butylcarbamoyl)-piperazinyl))-pentaneamide; the synthesis of which is described in EP 0541168. RO 31-8959 which is compound XVII as described in Roberts, N. A. et al., *Science* 248,358 (1990) is synthesized according to EP 0346847.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI.

EXAMPLE 1

N-(2'(R)-hydroxy-1'(S)-indanyl)-2(R)-phenylmethyl-4 (S)-hydroxy-5-[3'''-(methyl)butyl-(4''-(amino)phenylsulfonyl)]amino-pentaneamide

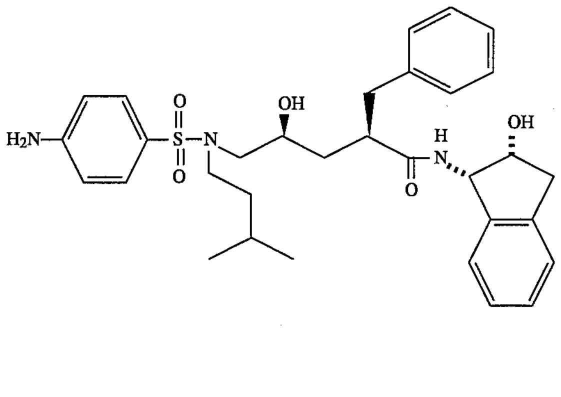

Step 1

Preparation of N-(2'(R)-hydroxy-1'(S)-indanyl)-2(R)-phenylmethyl 4(S)-hydroxy-5-[3''-(methyl)butyl]amino-pentaneamide N',O'-dimethyl acetal A mixture of epoxide 1 (2.0 g, 5.30 mmol) and isoamylamine (0.57 g, 6.52 mmol) was refluxed in isopropanol (20 mL) for 16 h. The solution was concentrated and purified by flash chromatography (3% methanol/chloroform saturated with ammonia) to yield 2 (2.3 g, 4.95 mmol) as a clear liquid.

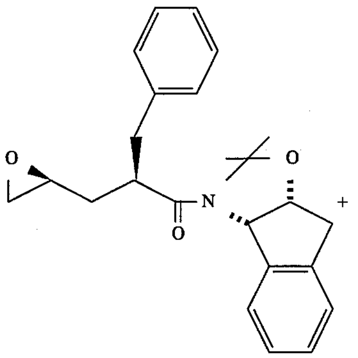

1

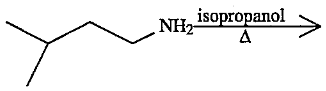

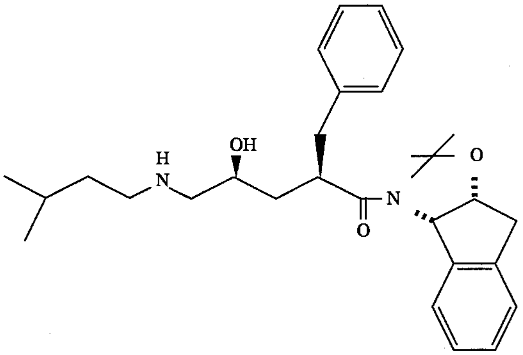

2

Step 2

Preparation of N-(2'(R)-hydroxy-1'(S)-indanyl)-2(R)-phenylmethyl-4(S)-hydroxy-5-[3''-(methyl) butyl]amino-pentaneamide hydrochloride A solution of 2 (2.3 g, 5.0 mmol) in isopropanol (50 mL) was cooled to 0° C. and saturated with anhydrous HCl. The solution was stirred and allowed to gradually warm to room temperature over 4 h, at which time it was concentrated. The resulting white hydrochloride salt was then diluted with ethyl acetate (20 mL), poured into saturated $NaHCO_3$ ( 100 mL), and washed with ethyl acetate (1×150 mL). The organic layer Was dried ($MgSO_4$), and concentrated to give a crude white solid which was purified by flash chromatography (5% methanol/ethyl acetate). The resulting solid was diluted with ethyl acetate, cooled to 0° C., and treated with anhydrous HCl to yield 3 (0.75 g, 1.63 mmol) as a white solid.

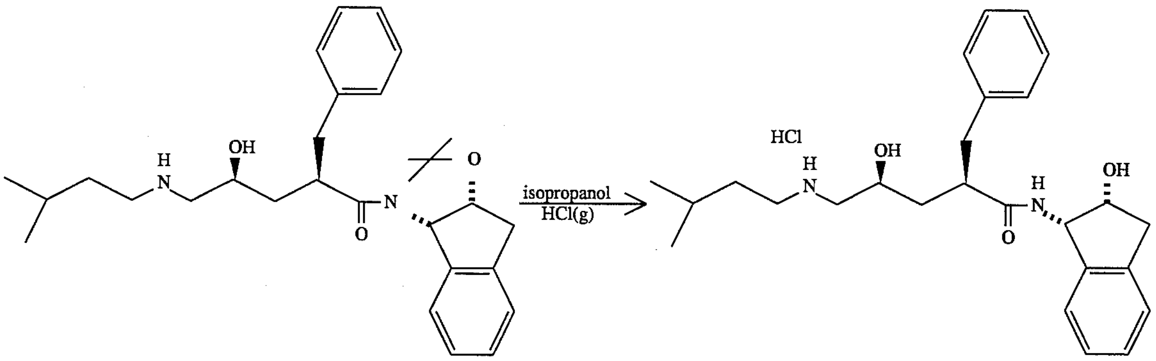

2 3

Step 3

Preparation of N-(2'(R)-hydroxy-1'(S)-indanyl)-2(R)-phenylmethyl-4(S)-hydroxy-5-[(3'''-(methyl)butyl)-(4''-(nitro)phenylsulfonyl)] amino-pentaneamide To a stirred solution of 3 (100 mg, 0.217 mmol) in dichloromethane (3 mL) at 0° C. was added triethylamine (48.6 mg, 0.067 mL, 0.477 mmol) and 4-nitrobenzenesulfonyl chloride (45 mg, 0.236 mmol). The solution was warmed to room temperature and stirred for 48 h at which time it was diluted with dichloromethane and washed with saturated $NaHCO_3$ (2×25 mL). The organic layer was dried ($MgSO_4$), concentrated, and recrystallized (ethyl acetate) to give 4 (74 mg, 0.121 mmol) as a white solid m.p. 217°–219° C.

Analysis calculated for $C_{32}H_{39}N_3O_7S$ 0.10 $CHCl_3$ C, 62.02; H, 6.34; N, 6.76; MWT, 621.69; Found: C, 63.26; H, 6.34; N, 6.89.

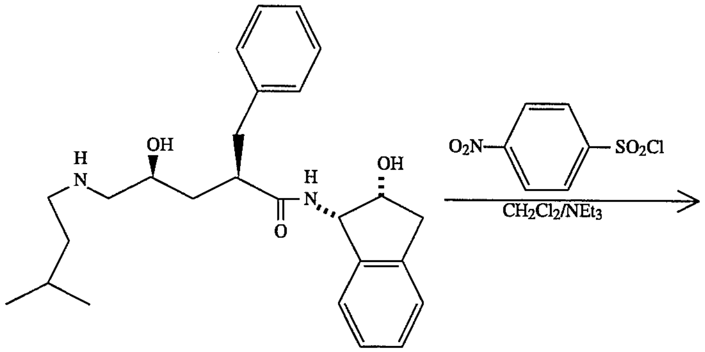

3

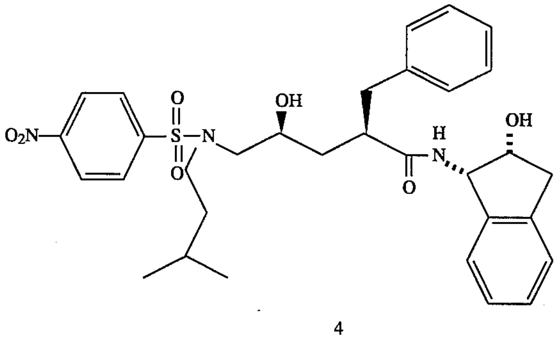

4

Step 4

Preparation of N-(2'(R)-hydroxy-1'(S)-indanyl)-2(R)-phenylmethyl-4(S)-hydroxy-5-[(3'''-(methyl)butyl)-(4'-(amino)phenylamino-pentaneamide A solution of 4 (40 mgs, 0.066 mmol) in tetrahydrofuran (5 mL) was stirred under Argon for 15 minutes. Palladium (10%) on activated carbon (6 mg) was added and the mixture was stirred for 15 minutes under Argon. The reaction vessel was then placed under a hydrogen filled balloon and stirred for 16 h. The mixture was diluted with tetrahydrofuran and filtered through celite. The filtrate was concentrated and recrystallized (ethyl acetate) to yield 5 (33 mg, 0.057 mmol) as a white solid m.p. 205°–207° C.

Analysis calculated for $C_{32}H_{41}N_3O_5S$ 0.10 $CHCl_3$ C, 65.16; H, 7.00; N, 7.10; MWT, 591.70; Found: C, 65.25; H, 6.98; N, 7.02.

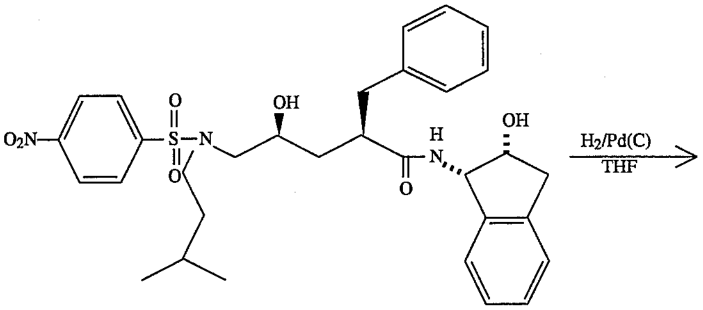

4

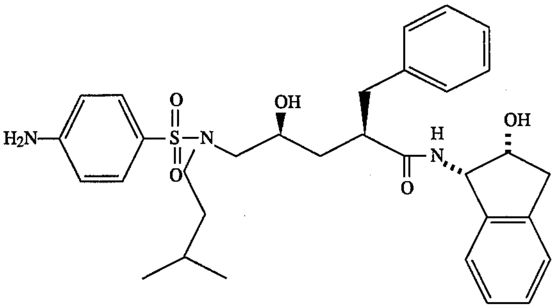

5

EXAMPLE 2

Preparation of N-(2'(R)-hydroxy-1'(S)-indanyl)-2(R)-phenylmethyl-4(S)-hydroxy-5-[((2''',2-'''dimethyl)propyl)-(4''-(methyl)-phenylsulfonyl)] amino-pentaneamide

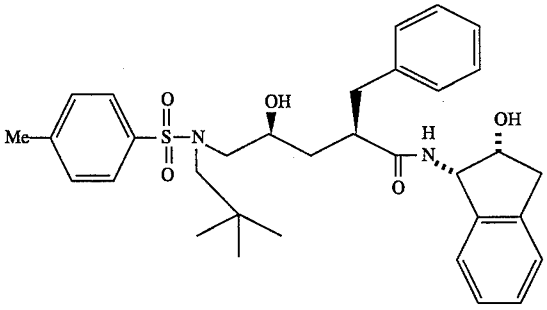

Step 1

Preparation of N-(2'(R)-hydroxy-1'(S)-indanyl)-2(R)-phenylmethyl-4(S)-hydroxy-5-((2'',2''-dimethyl)propyl)-amino-pentaneamide-N,O-dimethyl acetal

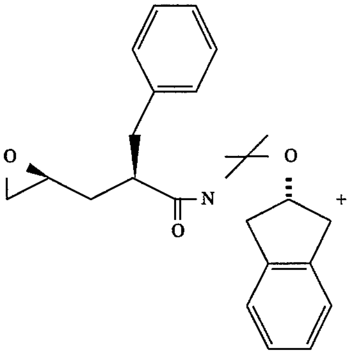

1

-continued

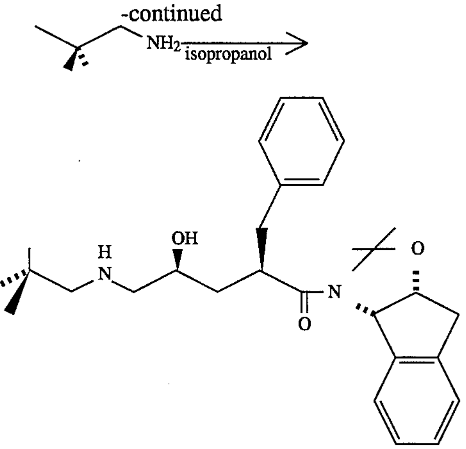

6

A mixture of epoxide 1 (1.5 g, 3.97 mmol) and neopentyl amine (0.42 g, 0.56 mL, 4.77 mmol) were refluxed in isopropanol (8 mL) for 16 h. The solution was concentrated to yield crude product 6 (1.93 g, 4.15 mmol) as a white solid. This material was used without further purification.

Step 2

Preparation of N-(2'(R)-hydroxy-1'(S)-indanyl)-2(R)-phenylmethyl-4(S)-hydroxy-5-((2'',2''-dimethyl)-propyl)amino-pentaneamide

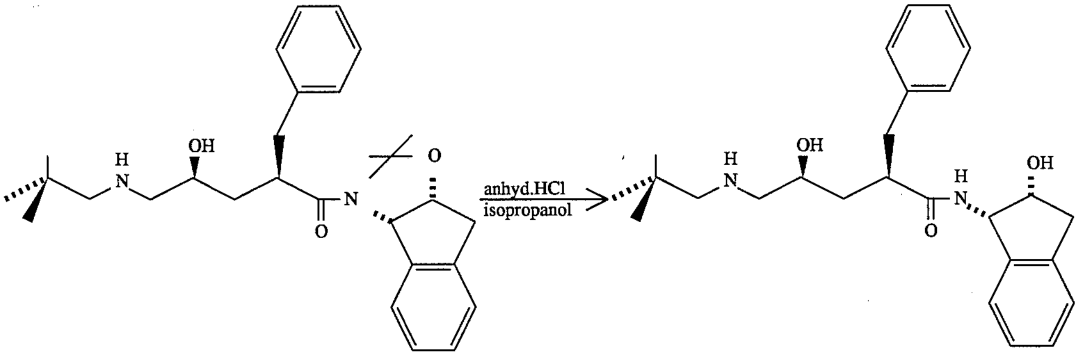

6 7

A solution of 6 (1.84 g, 3.97 mmol) in isopropanol (5 mL) was cooled to 0° C. and saturated with anhydrous HCl. The solution was stirred and allowed to gradually warm to room temperature over 3 h, at which time it was concentrated. The resulting white hydrochloride salt was then diluted with ethyl acetate, and washed with saturated $NaHCO_3$ (2×30 mL). The organic layer was dried ($MgSO_4$) and concentrated to give a crude white solid which was purified by flash chromatography (5% methanol/ethyl acetate) to yield 7 (1.45 g, 3.41 mmol, 86%) as a white solid.

Step 3

Preparation of N-(2'(R)-hydroxy-1'(S)-indanyl)-2(R)-phenylmethyl-4(S)-hydroxy-5-[((2''' ,2'''-dimethyl)propyl)-(4''-(methyl)phenylsulfonyl)] amino -pentaneamide

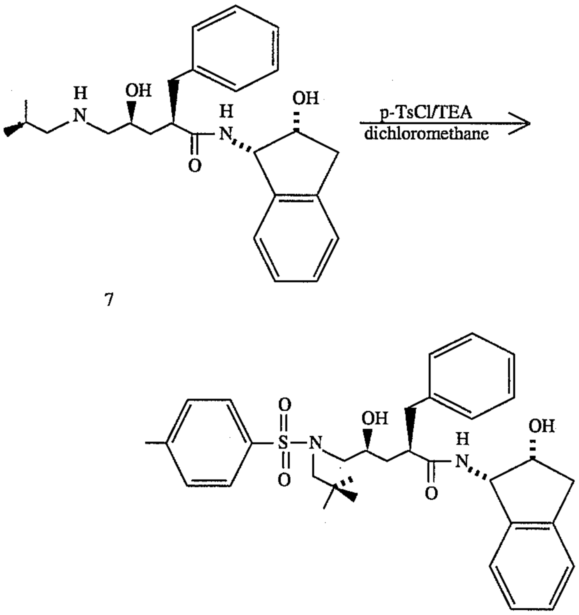

7

8

To a stirred solution of 8 (100 mg, 0.236 mmol) in dichloromethane (2 mL) at 0° C. was added triethylamine (0.039 mL, 0.283 mmol) and p-toluenesulfonyl chloride (45 mg, 0.236 mmol). The solution was warmed to room temperature and stirred for 16 h at which time it was diluted with dichloromethane and washed with saturated $NaHCO_3$ (2×25 mL). The organic layer was dried ($MgSO_4$), concentrated, and purified by flash chromatography (30% ethyl acetate/hexanes) to give the title compound (123 mg, 0.213 mmol, 90%) as a white solid m.p. 70°–73° C.

Analysis calculated for $C_{33}H_{42}N_2O_5S$ C, 68.48; H, 7.31; N, 4.84; MWT, 578.78; Found: C, 68.29; H, 7.50; N, 4.86.

EXAMPLE 3

Using the same methods as described in Example 1, Steps 1–3, the sulfonamides listed in Table 1 were prepared.

EXAMPLE 4

Preparation of N-(2'(R)-hydroxy-1'(S)-indanyl)-2(R)-phenylmethyl-4(S)-hydroxy-5-[((2''(RS) -tetrahydrofuryl)methyl)-(phenylmethyl) aminocarbonyl]amino-pentaneamide

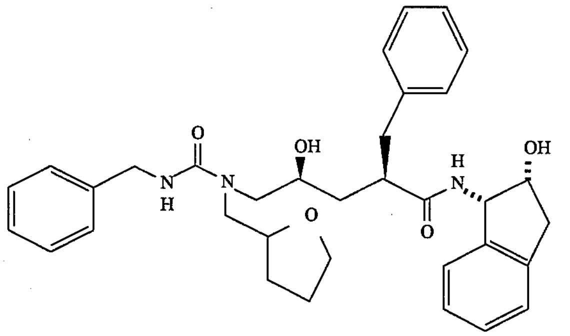

Step 1

Preparation of N-(2'(R)-hydroxy-1'(S)-indanyl)-2(R)-phenylmethyl-4(S)-hydroxy-5-[((2''(RS) -tetrahydrofuryl)methyl)-(phenylmethyl)-aminocarbonyl]amino-pentaneamide N',O'-dimethylacetal

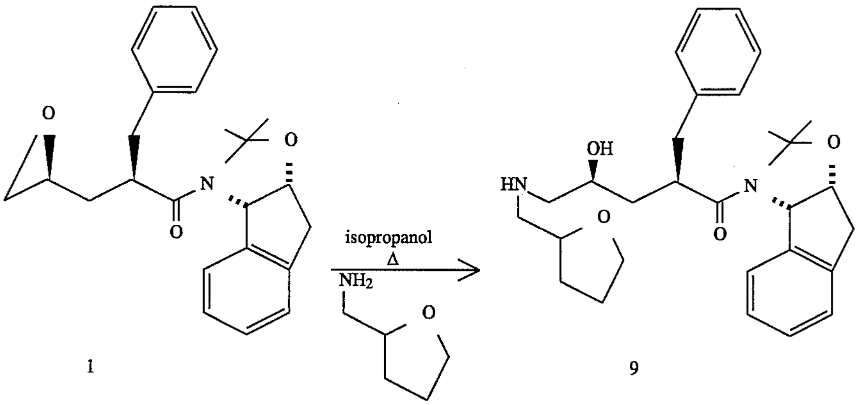

1 9

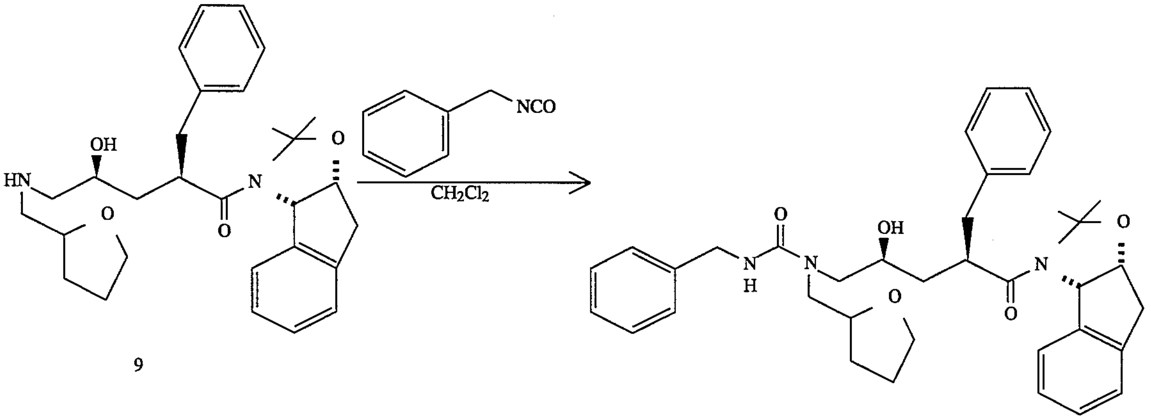

9 10

The protected indan epoxide 1 (100 mg, 0.265 mmol.) was refluxed with (RS)-tetrahydrofurfurylamine (500 microliters) in isopropanol overnight. After 16 h the reaction was evaporated and the residual oil azeotroped with toluene (3×10 mL). The yellow oil that remained was dissolved in methylenechloride followed by the addition of benzyl isocyanate (1.1 eq.). The reaction was stirred at room temperature overnight. After evaporation of the crude reaction left an oil that was dissolved in chloroform and placed on a 1 mm. prep TLC plate. The plated was developed in a 95/5 chloroform/methanol solvent system. The major product band was collected, extracted from the silica with 90/10 chloroform/methanol, filtered and evaporated to give a solid.

Step 2

Preparation of N-(2'(R)-hydroxy-1'(S)-indanyl)-2(R)-phenylmethyl-4(S)-hydroxy-5-[((2"(R,S) -tetrahydrofuryl)-methyl)-(phenylmethyl) aminocarbonyl]amino-pentaneamide

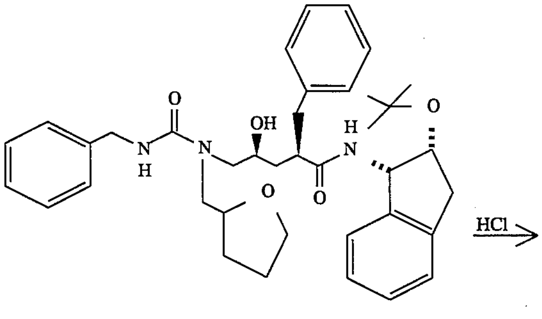

10

-continued

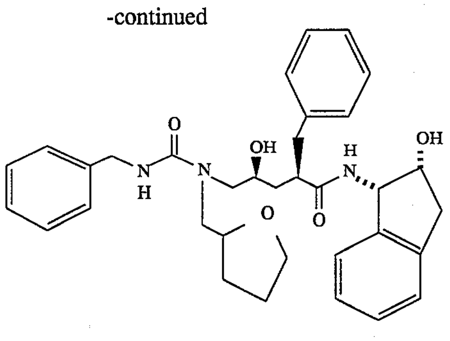

11

The purified product from above was dissolved in 15 mL of isopropanol and treated with 12M HCl (3 mL) and stirred until HPLC indicated no starting material. Yield 42.8 mg (m.p. 144°–147° C.)

Analysis calculated for $C_{34}H_{41}N_3O_5 0.15\ CHCl_3$ C, 69.56; H, 7.03; N, 7.13; MWT, 557.67; Found: C, 69.47; H, 7.09; N, 7.29.

EXAMPLE 5

Preparation of N-(2'(R)-hydroxy-1'(S)-indanyl)-2(R)-phenylmethyl-(S)-hydroxy-5-[((2''' -methyl)propyl)-(3''-(pyridyl)methyl)-aminocarbonyl]amino-pentaneamide

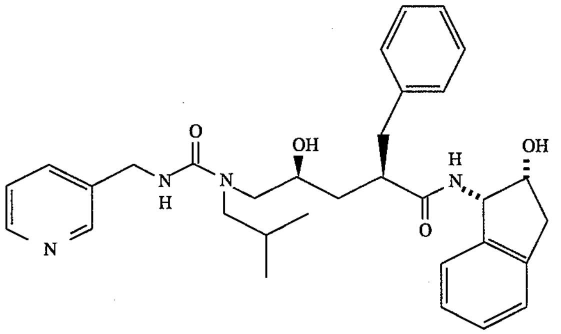

Step 1

Preparation of N-(2'(R)-hydroxy-1'(S)-indanyl)-2(R)-phenylmethyl-4(S)-hydroxy-5-[((2'' -tetrahydro-furyl)methyl)-(phenylmethyl) aminocarbonyl]amino-pentaneamide aminocarbonyl]amino-pentaneamide N',O'-dimethylacetal

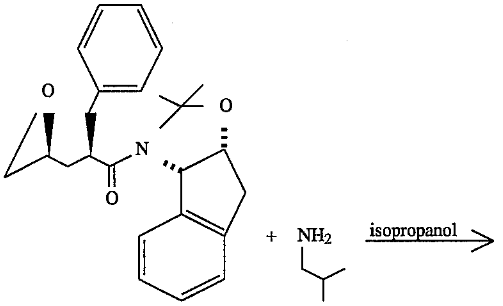

1

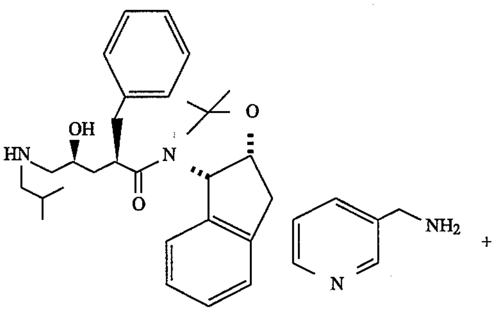

12

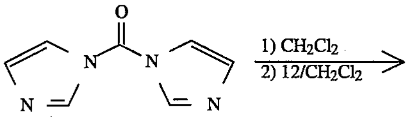

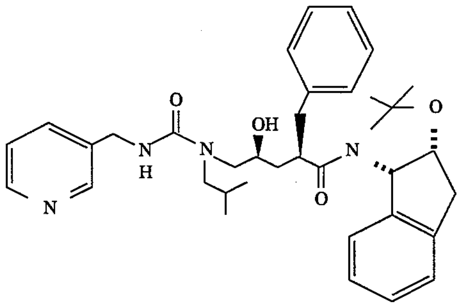

13

The protected indane epoxide 1 (100 mg, 0.265 mmol) was refluxed with isobutylamine (0.50 mL) in isopropanol overnight. The reaction was evaporated and the residue azeotroped with toluene (3×10 mL). A portion of the yellow oil (50 mg) that remained was dissolved in methylenechloride and stored in a stoppered round bottom flask. In a separate flask 3-aminomethylpyridine was dissolved in methylene-chloride and cooled to 0° C. Carbonyldiimidazole (CDI) was added and the reaction stirred for 30 min. The CDI reaction mixture was then added to the flask containing the indanamine 12. The coupling reaction was allowed to proceed at room temperature overnight. After evaporation the crude reaction product was dissolved in chloroform and placed on a 1 mm. prep TLC plate. The plated was developed in a 90/10 chloroform/methanol solvent system. The major product band was collected, extracted from the silica with 85/15 chloroform/methanol, filtered and evaporated to give a solid which was used directly in the next step.

Step 2

Preparation of N-(2'(R)-hydroxy-1'(S)-indanyl)-2(R)-phenylmethyl-4(S)-hydroxy-5-[((2''-methyl)propyl)-(3''-(pyridyl)methyl)aminocarbonyl]amino-pentaneamide

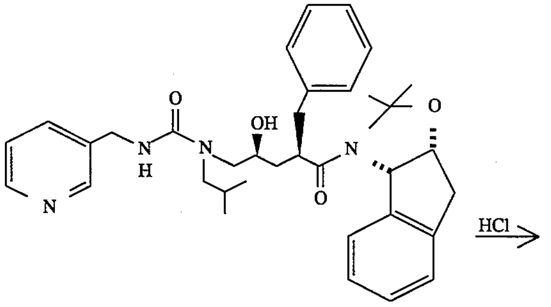

13

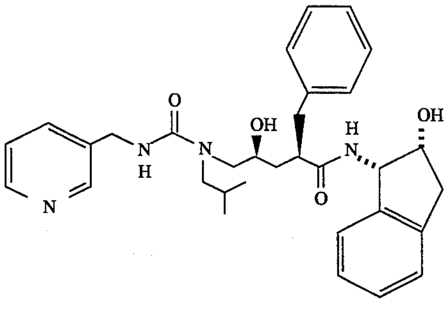

14

The purified product from above 13 was dissolved in 15 mL of isopropanol to which 12M HCl (3 mL) was added. The reaction was monitored by HPLC. The desired product 14 was purified by prep TLC as described above. Yield 32.2 mg (m.p. 75°–79° C.).

Analysis calculated for $C_{32}H_{40}N_4O_4$ 0.60 $CHCl_3$ C, 63.53; H, 6.64; N, 9.09; MWT, 616.327; Found: C, 63.76; H, 6.68; N, 9.09.

EXAMPLE 6

Using the same methods as described in Examples 2 and 3, the ureas listed in Table 4 were prepared.

EXAMPLE 7

Preparation of N-(2'(R)-hydroxy-1'(S)-indanyl)-2(R)-phenylmethyl-4(S)-hydroxy-5-[((2''-methyl)propyl)-benzyloxycarbonyl]aminopentaneamide

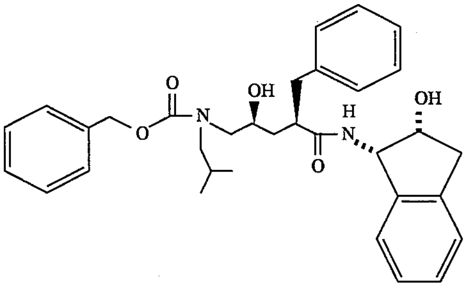

Step 1

Preparation of N-(2'(R)-hydroxy-1'(S)-indanyl)-2(R)-phenylmethyl-4(S)-hydroxy-5-[((2''-methyl)propyl)-benzyloxycarbonyl]amino-pentaneamide N',O'-dimethylacetal

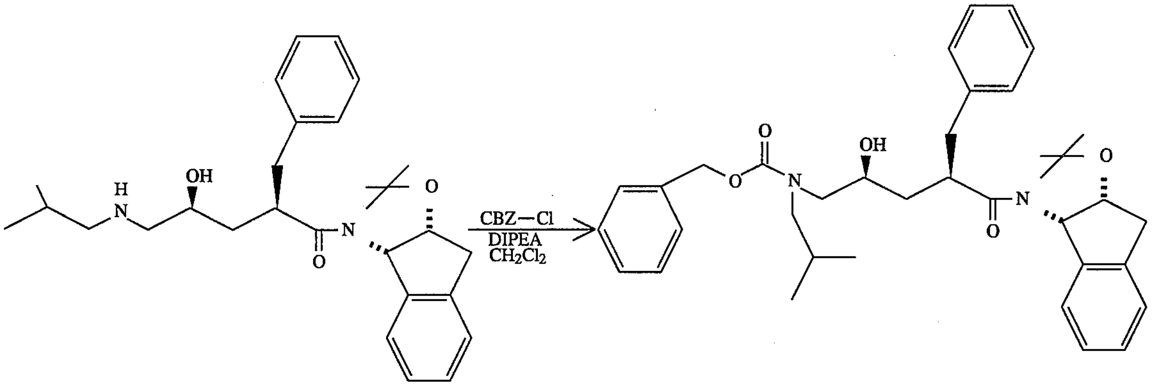
12 15
A mixture of 12 (100 mg, 0.232 mmol) prepared as described above, diisopropylethylamine (37.1 mg, 0.050 mL, 0.287 mmol) and benzyl chloroformate (39.4 mg, 0.033 mL, 0.23 1 mmol) were stirred in methylene chloride (6 mL) at room temperature for 16 h. The solution was concentrated and purified by preparative thin layer chromatography (5% methanol/chloroform). The product was used directly in the next step.
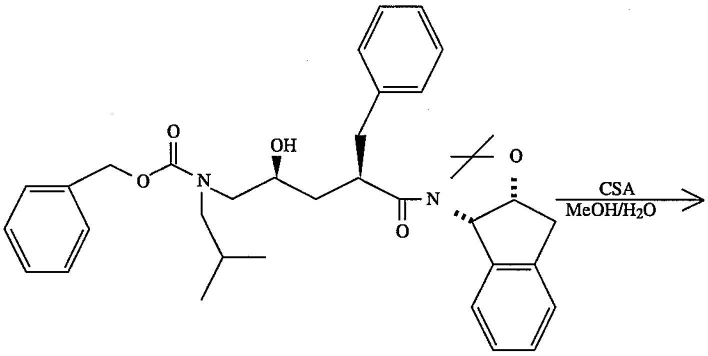
15
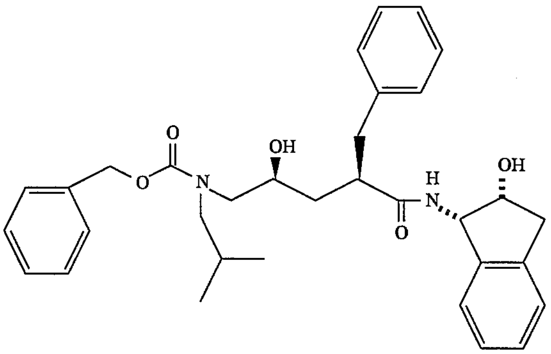
16

Step 2

Preparation of N-(2'(R)-hydroxy-1'(S)-indanyl)-2(R)-phenylmethyl-4(S)-hydroxy-5-[((2''-methyl)propyl)-benzyloxycarbonyl] amino-pentaneamide The acetonide 15 and camphorsulfonic acid were stirred in 10:1 methanol/water (13 mL) for 16 h. The solution was concentrated, diluted with ethyl acetate (15 mL), and washed with saturated $NaHCO_3$ (2×5 mL) and saturated NaCl (2×5 mL). The organic layer was dried ($Na_2SO_4$), concentrated, and purified by preparative thin layer chromatography (10% methanol/chloroform) to give 77 mg of a white solid (m.p. 119°–122° C.).

Analysis calculated for $C_{33}H_{40}N_2O_5$ C, 72.77; H, 7.40; N, 5.14; MWT, 544.69; Found: C, 72.58; H, 7.42; N, 5.19.

EXAMPLE 8

Preparation of N-(2'(R)-hydroxy-1'(S)-indanyl)-2(R)-phenylmethyl-4(S)-hydroxy-5-[((2''-methyl)butyl)-3'(S)-(tetrahydrofuranyloxy) carbonyl)-amino-pentaneamide

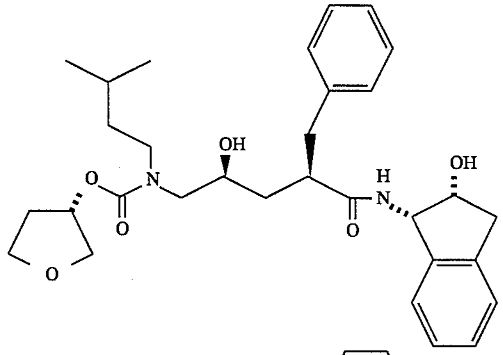

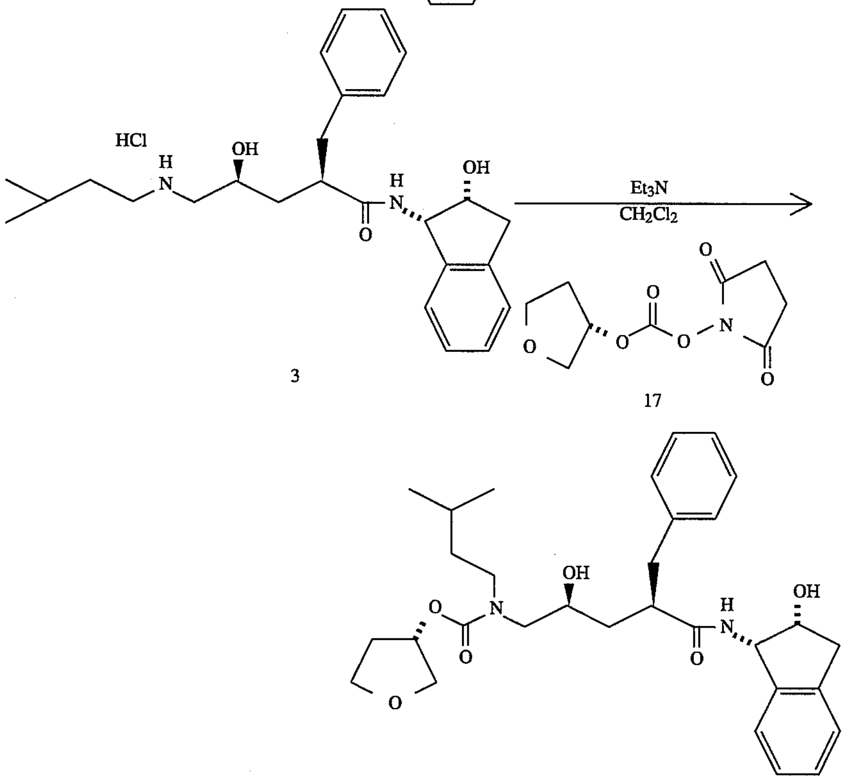

3

17

18

A solution of amine 3 prepared as described above, (30 mg, 0.067 mmol) in dichloromethane (3 mL) at 0° C. was treated with triethylamine (17 mg, 0.021 mL, 0.168 mmol) and then 17 (16 mg, 0.067 mL). The resulting solution was allowed to warm to room temperature and stirred for 16 h, at which time it was poured into saturated $NaHCO_3$ (20 mL). The biphasic system was then washed with dichloromethane (25 mL) and the organic extracts were dried ($MgSO_4$), and concentrated under reduced pressure to give a crude white solid. The solid was purified by recrystallization ($CH_2Cl_2$/hexanes) to give pure 18 (16 mg, 0.030 mmol) as white needles m.p. 153°–155° C.

EXAMPLE 9

Using the same methods as described in Examples 6 and 7, the carbamates listed in Table 2 were prepared.

EXAMPLE 10

Preparation of N-(2'(R)-hydroxy-1'(S)-indanyl)-2(R)-phenylmethyl-4(S)-hydroxy-5-[((2' "-methyl)propyl)-(cyclopentylmethyl)carbonyl] amino-pentaneamide

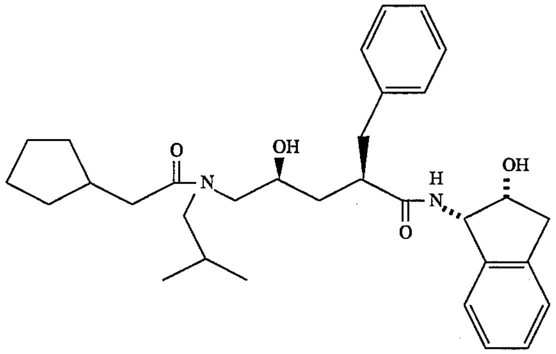

Step 1

Preparation of N-(2'(R)-hydroxy-1'(S)-indanyl)-2(R)-phenylmethyl-4(S)-hydroxy-5-[((2" '-methyl)propyl)-(cyclopentylmethyl)carbonyl] amino-pentaneamide N'O'-dimethylacetal

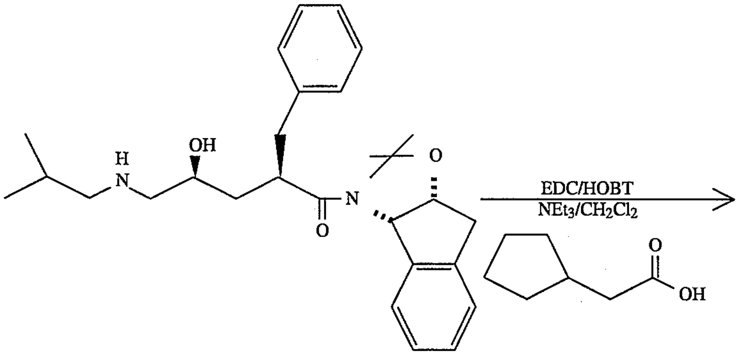

1

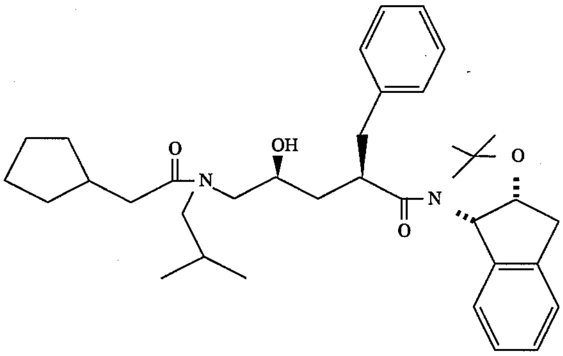

19

A mixture of 1 prepared as described above (100 mg, 0.232 mmol), 1-ethyl-3-(3-dimethylaminopropyl)carbodiimide-HCl (49 mg, 0.255 mmol), 1-hydroxybenzotriazole hydrate (35 mg, 0.255 mmol), triethylamine (73 mg, 0,100 mL, 0.717 mmol), and cyclopentylacetic acid (102 mg, 0.100 mL, 0.797 mmol) were stirred in methylene chloride (8 mL) at room temperature. After 24 hours the solution was diluted with methylene chloride and washed with 10% citric acid (3×25 mL), saturated $NaHCO_3$ (3×25 mL), and saturated NaCl (1×25 mL). The organic layer was dried ($Na_2SO_4$) and concentrated to an oil which was purified by preparative thin layer chromatography (5% methanol/chloroform).

Step 2

Preparation of N-(2'(R)-hydroxy-1'(S)-indanyl)-2(R)-phenylmethyl-4(S)-hydroxy-5-[((2"'-methyl)propyl)-(cyclopentylmethyl)carbonyl]amino-pentaneamide

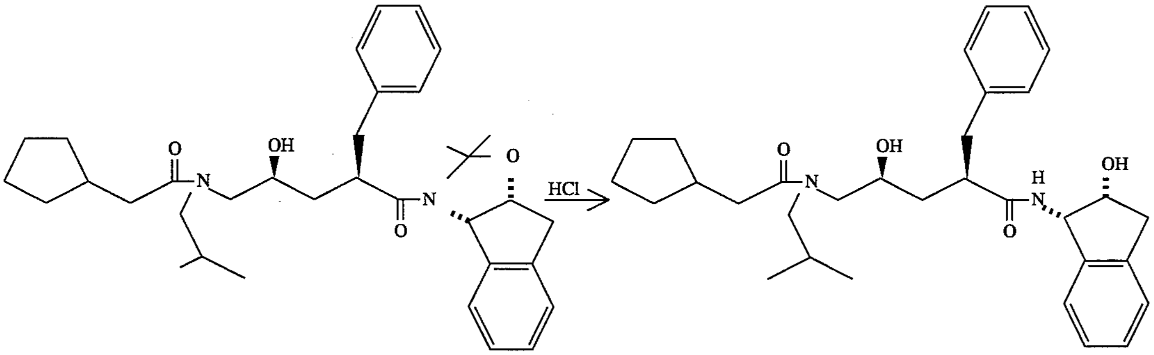

19

20

The acetonide 19 prepared from above was dissolved in isopropanol (10 mL) and treated with 12M HCl (3 mL). After 4 hours the solution was neutralized with 4N NaOH, concentrated, and the product was extracted into ethyl acetate. The organic layer was dried ($Na_2SO_4$) and concentrated. The crude product was purified by preparative thin layer chromatography (8% methanol/chloroform) to yield 20 (115 mg, 0.220 mmol) as a white solid (m.p.141°–145° C.).

Analysis calculated for $C_{32}H_{44}N_2O_4$0.01 $CHCl_3$ C, 73.66; H, 8.50; N, 5.37; MWT, 521.88; Found: C, 73.29; H, 8.42; N, 5.19.

EXAMPLE 11

Using the same methods as described in Example 9 the amides listed in Table 4 were prepared.

EXAMPLE 12

Preparation of Amide 21

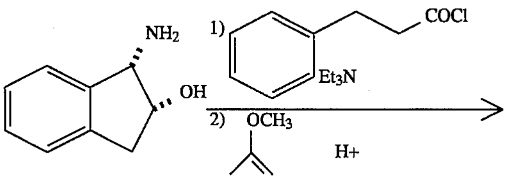

-continued

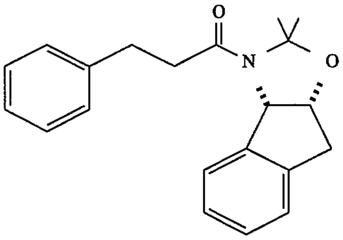

21

A solution of (–)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over minutes, while the internal temperature between 14°–24° C. with an ice-water cooling batch. After addition, the mixture was aged at 18° to 20° C. for 30 minutes and checked by HPLC analysis for the disappearance of (–)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation= 500 X dilution. Approximate retention times:

| retention time (min.) | identity |
|---|---|
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 21 (86.4%, 98 area % by HPLC). $^1H$ NMR (300.13 MHz, $CDCl_3$, major rotamer) δ7.36–7.14 (m, 9 H), 5.03 (d, J=4.4, 1 H), 4.66 (m, 1 H), 3.15 (m, 2 H), 3.06 (br s, 2 H), 2.97 (m, 2 H), 1.62 s (s, 3 H), 1.37 (s, 3 H); $^{13}C$ NMR (75.5 MHz, $CDCl_3$, major rotamer) $\delta_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

Anal. Calcd for $C_{21}H_{23}NO_2$: C, 78.47; H, 7.21; N, 4.36. Found: C, 78.65; H, 7.24; N, 4.40.

EXAMPLE 13

Preparation of Epoxide 1 Tosylate Method

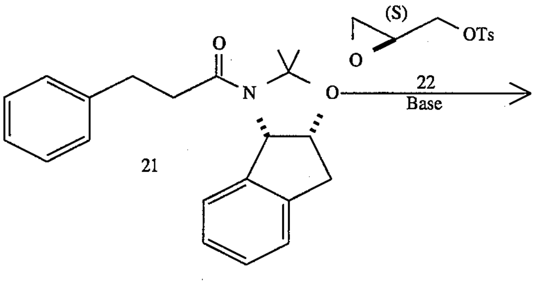

21

-continued

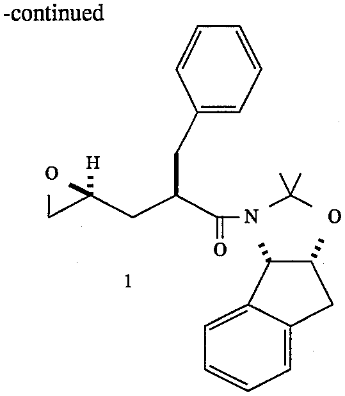
1

A solution of acetonide 21 (1000 g, 3.11 mol) and 2(S)glycidyl tosylate 22 (853 g, 3.74 mol, 1.2 equiv.) in 15.6 L of THF (KF =22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide ($LiN[(CH_3)_3Si]_2$)(2.6 L, 1.38 M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection=254 nm, sample preparation=100×dilution. Approximate retention times: retention time (min.) identity

| retention time (min.) | identity |
|---|---|
| 5.5 | amide 21 |
| 6.5 | glycidyl tosylate 22 |
| 13.5 | epoxide 1 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous $NaHCO_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 1 (61.2%, 98.7 area % of the major epoxide by HPLC). $^{13}C$ NMR (300 MHz, $CDCl_3$) δ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 14

Assay for Inhibition of Microbial Expressed HIV Protease

Inhibition studies of the reaction of the protease expressed in Escherichia coli with a peptide substrate [Val-Ser-Gln-Asn-(betanaphthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ul DMSO were added to 25 ul of the peptide solution in water. The reaction is initiated by the addition of 15 ul of 0.33 nM protease (0.11 mg) in a solution of 0.133 M Na acetate pH 5.5 and 0.26% bovine serum albumin. The reaction was quenched with 160 ul of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compound A showed $IC_{50}$ value of about 8–9 nM.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A compound of the formula

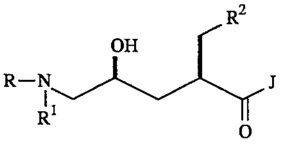

Formula I

Wherein

R is
- a) —V—$R^3$; wherein V is —C(O)—Q—, or —$SO_2$—Q—;

Q is
- a) absent, —O—, or —NH—, $R^1$ is
- a) hydrogen, or
- b) —$C_{1-5}$alkyl unsubstituted or substituted with one or more of
  - i) halo,
  - ii) hydroxy,
  - iii) $C_{1-3}$alkoxy,
  - iv) aryl unsubstituted or substituted with one or more of $C_{1-4}$alkyl, $C_{1-4}$alkoxy, nitro, amino, amido, carboxy, hydroxy, halo or aryl;
  - v) carboxyl;
- —$C_{3-5}$cycloalkyl, unsubstituted or substituted at the 3-position with $C_{1-4}$alkyl; or
- d) aryl unsubstituted or substituted with one or more of $C_{1-4}$alkyl, $C_{1-4}$alkoxy, nitro, amino, amido, carboxy, hydroxy, halo or aryl; and $R^2$ is
- a) phenyl unsubstituted or substituted with one or more of —OH or $C_{1-3}$ alkoxy; or
- b) $C_{5-7}$ cycloalkyl, unsubstituted or substituted with one or more of —OH or $C_{1-3}$ alkoxy;

$R^3$ is
- a) aryl unsubstituted or substituted with one or more of —$C_{1-4}$alkyl, oxo, amino or halo;
- b) $C_{1-4}$alkyl, unsubstituted or substituted once with aryl;
- c) $C_{3-5}$cycloalkyl, unsubstituted or substituted at the 3-position with $C_{1-4}$alkyl;

J is

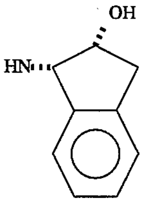

, or

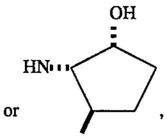

, or pharmaceutically acceptable salt thereof.

2. The compound of claim 1, wherein

R is
—V—$R^3$; wherein V is —C(O)—Q—, or —$SO_2$—Q—;

Q is
- a) absent, or —O—;

$R^1$ is
—$C_{1-5}$alkyl unsubstituted or substituted with one or more of
- i) aryl unsubstituted or substituted with one or more of $C_{1-4}$alkyl, $C_{1-4}$alkoxy, nitro, amino, amido, carboxy, hydroxy, halo or aryl;

$R^2$ is phenyl unsubstituted or substituted with one or more of —OH or $C_{1-3}$alkoxy;

$R^3$ is
- a) aryl unsubstituted or substituted with one or more of —$C_{1-4}$alkyl, oxo, amino or halo;
- b) $C_{1-4}$alkyl, unsubstituted or substituted once with aryl;

J is

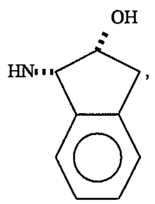
or a pharmaceutically acceptable salt thereof.
3. The compound
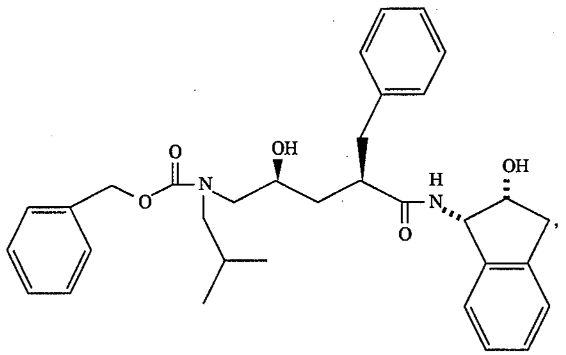
named N-(2'(R)-hydroxy-1'(S)-indanyl)-2(R)-phenylmethyl-4(S)-hydroxy-5-[((2''' -methyl)propyl)-benzyloxycarbonyl]-aminopentaneamide, or pharmaceutically acceptable salt thereof.
4. A method of inhibiting HIV protease, comprising administering an effective amount of a compound as in any of claims 1–3
* * * * *